United States Patent [19]

Wun et al.

[11] Patent Number: 5,733,736
[45] Date of Patent: Mar. 31, 1998

[54] MOTILITY CHANNEL PATHOGEN DETECTOR AND METHOD OF USE

[75] Inventors: Chun Kwun Wun, Palmer; Frank J. Torre, Springfield, both of Mass.

[73] Assignee: Springfield College, Springfield, Mass.

[21] Appl. No.: 767,165

[22] Filed: Dec. 16, 1996

[51] Int. Cl.$^6$ .................................................. G01N 33/567
[52] U.S. Cl. ........................... 435/7.21; 435/30; 435/515
[58] Field of Search ....................... 435/7.21, 30; 436/515

[56] References Cited

U.S. PATENT DOCUMENTS

| | | | |
|---|---|---|---|
| 3,715,280 | 2/1973 | Farmer, III | 435/34 |
| 3,728,228 | 4/1973 | Duranty | 435/288.3 |
| 3,769,171 | 10/1973 | Grimes et al. | 435/243 |
| 3,769,936 | 11/1973 | Swanson et al. | 119/65 |
| 3,816,264 | 6/1974 | Winter et al. | 435/288.3 |
| 3,904,482 | 9/1975 | Mehl | 435/34 |
| 3,912,596 | 10/1975 | Haque et al. | 435/309.1 |
| 3,929,583 | 12/1975 | Sharpe et al. | 435/288.5 |
| 4,039,253 | 8/1977 | Jain | 359/267 |
| 4,042,463 | 8/1977 | Haque et al. | 435/252.1 |
| 4,053,362 | 10/1977 | Sforza | 435/243 |
| 4,072,577 | 2/1978 | Hirshaut | 435/252.1 |
| 4,204,045 | 5/1980 | Kjellander et al. | 435/288.5 |
| 4,228,243 | 10/1980 | Fizuka | 435/294.1 |
| 4,294,924 | 10/1981 | Pepicelli et al. | 435/30 |
| 4,513,280 | 4/1985 | Hannan et al. | 340/632 |
| 4,530,907 | 7/1985 | Peterson et al. | 435/32 |
| 4,563,418 | 1/1986 | Ward, Jr. | 435/7.3 |
| 4,587,213 | 5/1986 | Malecki | 435/39 |
| 4,668,633 | 5/1987 | Walton, Jr. | 435/305.2 |
| 4,709,819 | 12/1987 | Lattuada et al. | 206/524.8 |
| 4,728,607 | 3/1988 | Dorn et al. | 435/34 |
| 4,743,556 | 5/1988 | Ervin | 435/305.1 |
| 4,912,037 | 3/1990 | Lemonnier | 435/34 |
| 4,920,063 | 4/1990 | Ward, Jr. | 435/7.35 |
| 4,923,804 | 5/1990 | Ley et al. | 435/38 |

(List continued on next page.)

OTHER PUBLICATIONS

Warburton et al, JAOAC Int., vol. 78(1), 1995, pp. 59–68.
Ederer, GM et al, J. Clin. Microbiol., Sep., Vol. 2(3), pp. 266–267, 1975.
Scotland, SM et al, J. Clin. Path, vol. 45, pp. 1075–1078, 1992.
Feng,P et al.J. Clin. Microbiol, Nov., vol. 34(11), pp. 2856–2859, 1996.
Smith, EG et al, Am. J. Clin. Path., Jan., vol. 75(1), pp. 88–91, 1981.
SwaminAthan, B et al., J. Food Sci, 1978, vol. 43(5), pp. 1444–1447.
Kwapinski, JBG, Methodology of Immunochemical and Immunological Research, 1972, Chapter 7, pp. 353–359, especially p. 354.

*Primary Examiner*—James C. Housel
*Assistant Examiner*—Ginny Allen Portner
*Attorney, Agent, or Firm*—Malcolm J. Chisholm, Jr.

[57] ABSTRACT

A motility channel pathogen detector and method of use of the detector are disclosed for detecting a target motile pathogen in a test sample of potential pathogens. The motility channel pathogen detector includes: a dish having a base and walls arising from the base to define a motility channel; an anti-serum end of the motility channel; an inoculation end of the motility channel opposed to the anti-serum end; and opposed channel walls that cooperate to define the motility channel between the anti-serum and inoculation ends of the channel. A growth medium is positioned in the motility channel and an anti-serum that biologically interacts with the target motile pathogen is positioned in the growth medium in the anti-serum end so that the anti-serum diffuses in the growth medium to form an anti-serum front between the channel walls. The sample of potential pathogens is inoculated in the growth medium adjacent the inoculation end so that any target motile pathogen moves towards, contacts and accumulates at the anti-serum front to form a visible detection line adjacent the anti-serum front. In one embodiment the target motile pathogen is a serotype of *Escherichia coli* bacteria generally known as "*E. coli* 0157:H7", and the anti-serum is *E. coli* H7 anti-serum which restricts motility of the pathogen.

21 Claims, 1 Drawing Sheet

U.S. PATENT DOCUMENTS

| | | | |
|---|---|---|---|
| 4,928,501 | 5/1990 | Negishi | 62/406 |
| 5,026,649 | 6/1991 | Layman et al. | 435/284 |
| 5,061,621 | 10/1991 | Perlman | 435/30 |
| 5,084,565 | 1/1992 | Parodos et al. | 536/27 |
| 5,123,332 | 6/1992 | Thayer et al. | 92/103 M |
| 5,132,229 | 7/1992 | Ward, Jr. et al. | 435/28 |
| 5,156,948 | 10/1992 | Christensen et al. | 435/5 |
| 5,164,298 | 11/1992 | Lingwood et al. | 435/7.37 |
| 5,168,063 | 12/1992 | Doyle et al. | 435/240.27 |
| 5,188,946 | 2/1993 | Ward, Jr. et al. | 435/6 |
| 5,189,151 | 2/1993 | Baudry et al. | 536/24.32 |
| 5,272,084 | 12/1993 | O'Connell et al. | 435/395 |
| 5,296,375 | 3/1994 | Kricka et al. | 435/2 |
| 5,354,568 | 10/1994 | Beader et al. | 426/332 |
| 5,354,661 | 10/1994 | Doyle et al. | 435/7.37 |
| 5,374,551 | 12/1994 | Bochner | 435/252.1 |
| 5,403,741 | 4/1995 | Holbrook | 435/288.2 |
| 5,405,773 | 4/1995 | Fung et al. | 435/243 |
| 5,415,997 | 5/1995 | Atrache et al. | 435/7.35 |
| 5,475,098 | 12/1995 | Hall et al. | 536/23.7 |
| 5,512,282 | 4/1996 | Krivan et al. | 424/169.1 |
| 5,552,288 | 9/1996 | Christensen et al. | 435/7.9 |
| 5,552,294 | 9/1996 | Thorne | 435/7.32 |

MOTILITY CHANNEL PATHOGEN DETECTOR AND METHOD OF USE

TECHNICAL FIELD

The present invention relates to apparatus and methods for detection of microbial pathogens, and especially relates to an apparatus and method for detecting motile pathogens such as a serotype of *Escherichia coli* bacteria generally known as "*E. coli* 0157:H7".

BACKGROUND OF THE INVENTION

It is well known that so-called "Shiga-like" toxins produced by *E. coli* 0157:H7 are a cause of a spectrum of diseases in humans ranging from mild and bloody diarrhea to life threatening hemorrhagic colitis and hemolytic uremic syndrome ("HUS"). HUS is a leading cause of acute renal failure, and infants, young children and the elderly are most susceptible. Recent outbreaks of *E. coli* 0157:H7 have been associated with contamination of ground beef sandwiches at "fast-food" restaurants and contaminated food at nursing homes. In one well known nursing home incident, HUS occurred in approximately 24% of the residents, most of whom died. Fear of contamination of meat products in school lunch programs is but one of many pressing public health concerns related to the extraordinary toxicity of *E. coli* 0157:H7 bacteria.

Detection of the presence of the *E. coli* 0157:H7 bacteria is therefore a primary concern in treating individuals suspected of being infected, as well as in testing food products to eliminate or control contamination and infection. Known detection methodologies can be generally grouped into four categories. In the first category, standard bacteria culture techniques are employed wherein a sample of a potential pathogen is incubated and grown for a specific time under controlled circumstances in a well known procedure. The resulting culture is then treated to detect the presence of *E. coli* 0157:H7 based on specific biochemical characteristics of the pathogen. The two most commonly used characteristics are the inability of *E. coli* 0157:H7 to ferment sorbitol within 24 hours, and the lack of β-glucuronidase activity in *E. coli* 0157:H7. While this category of detection has achieved satisfactory results, it is time consuming to grow and treat the sample cultures, typically taking between 3–4 days; it takes skilled laboratory technicians to implement the treatment aspects; and the results are susceptible to frequent false negative reports due to failure to detect very small, yet potentially lethal amounts of *E. coli* 0157:H7 bacteria present in the sample. U.S. Pat. No. 5,084,565 to Parodos et al. describes such test methods in more detail at Col. 1, line 66–Col. 2, line 23.

A second category of detection methodologies for *E. coli* 0157:H7 is use of genetic or DNA "probes" to detect segments of a DNA molecule of the *E. coli* 0157:H7 that produce its Shiga-like toxins and verotoxins, or to identify markers associated with toxin production. Such methods utilize synthetically or biologically produced nucleic acid fragments (DNA or RNA) which by design or selection contain specific nucleotide sequences that allow them to hybridize under specific conditions with target nucleic acids segments, such as the nucleic acid segments responsible for producing the Shiga-like toxins associated with the *E. coli* 0157:H7 bacteria. Typically, implementation of a gene probe test involves cultivation and enrichment of a test sample of a potential pathogen; the enriched bacteria are lysed and both a capture and reporter gene probe are added to the sample; and after a period of time adequate for hybridization of the probe to any target nucleic acid segments, the resulting capture and reporter probes are extracted and treated with chromogenic compounds that ultimately develop a color indicative of the presence or absence of the target nucleic acid segments, such as the segment that produces the Shiga-like toxins. The aforesaid U.S. Patent to Parodos et al. describes such a test in more detail at Col. 3, line 50–Col. 4, line 26, and contrasts usage of such gene probes favorably with the aforesaid culture/biochemical characteristics category, especially in elimination of false negatives. However, the use of gene probes involves approximately 2–3 days; skilled technicians to implement the tests; a quality laboratory environment for implementing the tests; and substantial costs to obtain the probes.

The third category is characterized as immunological detection of the Shiga-like toxins, and involves immunoblotting with polyclonal antibodies for detection verotoxins of *E. coli* 0157:H7, or with monoclonal antibodies for detection of a 0157 antigen. As described in more detail in U.S. Pat. No. 5,168,063 to Doyle et al. at Col. 5, lines 29–Col. 8, line 19, such immunological detection methods may include production of a hybridoma generated monoclonal antibody specific to *E. coli* 0157:H7; binding the antibody to an adsorptor substrate; exposing a sample of a potential pathogen to the substrates; and using a quantitative and comparative assay (such as an enzyme-linked immuno-sorbent assay ("ELISA")) to test for the presence of *E. coli* 0157:H7. While such techniques have a high degree of accuracy and can reduce the total detection time to about two days, implementation of such methods requires a skilled technician to perform the steps; involves a substantial cost to acquire the specific antibodies and assay components; and requires a high quality laboratory environment to properly carry out such a test.

The fourth category of detection methodologies is detection of Shiga-like toxin producing *E. coli* 0157:H7 based on vero-cell toxicity. Verotoxin (VT) in a supernatant bacterial broth culture, in fecal filtrates, and in polymyxin-releasable VT from polymyxin B-treated bacterial cultures have been assayed by vero cell toxicity testing. Several different antigenic types or variants of toxin have been detected by this procedure and it is considered one of the most sensitive for testing for the presence of vero toxin producing *E. coli* 0157:H7. However, vero cell toxicity testing is excessively time consuming, and is therefore of limited application, and has not been generally used in routine assessment procedures.

As can be seen, none of the known detection methodologies have gained wide-spread acceptance where such a test could be of most value; namely in non-laboratory, field testing, such as in food processing plants. The above four methodologies are generally applied to detect the presence of a Shiga-like toxin producing pathogen in a human victim, after infection and the onset of symptoms, and therefore after contamination and an out break of a potentially fatal, contagious disease. In contrast, implementation of a high frequency, low cost routine testing methodology in food processing plants could detect the presence of such pathogens prior to their being distributed to consumers so that steps could be taken to prohibit contamination of humans. Unfortunately, no such low cost, reliable testing methodology for field applications is presently known.

Accordingly, it is the general object of the present invention to provide an improved pathogen detector and method of use that overcomes the implementation time, high level of technical skill, and cost problems associated with the prior art.

It is a more specific object to provide a pathogen detector and method of use that can detect the presence of E. coli 0157:H7 bacteria within 18–24 hours.

It is another specific object to provide a pathogen detector and method of use that can be implemented by a person with limited technical skill.

It is yet another object of the present invention to provide a pathogen detector and method of use that can be readily implemented in an environment of a food processing plant.

The above and other objects and advantages of this invention will become more readily apparent when the following description is read in conjunction with the accompanying drawings.

SUMMARY OF THE INVENTION

A motility channel pathogen detector and method of use of the detector are disclosed for detecting a target motile pathogen in a test sample of potential pathogens. In a preferred embodiment, the motility channel pathogen detector includes: a dish having a base and walls arising from the base to define a motility channel; an anti-serum end of the motility channel; an inoculation end of the motility channel opposed to the anti-serum end; and opposed channel walls that cooperate to define the motility channel between the anti-serum and inoculation ends of the channel; a growth medium in the motility channel; an anti-serum that biologically interacts with a motile pathogen, the anti-serum being positioned in the growth medium in the anti-serum end so that the anti-serum diffuses in the growth medium to form an anti-serum front between the channel walls; and, a target motile pathogen positioned in the growth medium adjacent the inoculation end so that the motile pathogen moves towards, contacts and accumulates at the anti-serum front to form a visible detection line adjacent the anti-serum front.

A method of use of the motility channel pathogen detector includes the steps of: positioning on a growth medium in an anti-serum end of a motility channel in a motility channel pathogen detector an anti-serum for biologically interacting with a motile pathogen so that the anti-serum diffuses through the growth medium to form an anti-serum front in the motility channel; positioning a sample of a motile pathogen on the growth medium adjacent an inoculation end of the motility channel; incubating the detector at 22°–37° Centigrade for between 8–24 hours; and viewing the anti-serum front for detecting accumulation of the motile pathogen into a visible detection line.

As can be readily seen, use of the motility channel pathogen detector of the present invention allows a user to simply apply an anti-serum for specific target motile pathogens such as E. coli 0157:H7, Salmonella, etc. to the anti-serum end of the motility channel in the detector; to then apply a potential pathogen sample adjacent the inoculation end of the motility channel; to next incubate the detector in a common oven for a short period of time; and finally to view the motility channel for accumulation of a pathogen with which the anti-serum interacts to stop further motion of the pathogen, thereby causing the accumulated, immobile pathogens to form a visible detection line. For example if it is desired to detect E. coli 0157:H7 as a target pathogen, an anti-serum commonly referred to as "E. coli H7 anti serum" that is specific to E. coli 0157:H7 is used. E. coli H7 anti-serum attaches to flagella of the E. coli 0157:H7 pathogen, thereby immobilizing the bacteria so that it accumulates into a visible detection line at the anti-serum front. If no E. coli 0157:H7 are present in the sample, then no detection line will appear.

In more specific embodiments of the invention, one detector may include a plurality of channels for detecting different pathogens during one test; the growth medium may be specially prepared and the detector specially constructed to enhance motility of the pathogens, thereby shortening the time required for the pathogens to accumulate into a visible line; and anti-sera of different motile pathogens may be positioned between the anti-serum front and the inoculation end to reduce the possibility of any non-target motile pathogens interfering with movement of the target pathogen all the way to the anti-serum front.

DESCRIPTION OF THE PREFERRED EMBODIMENTS

Figure 1:
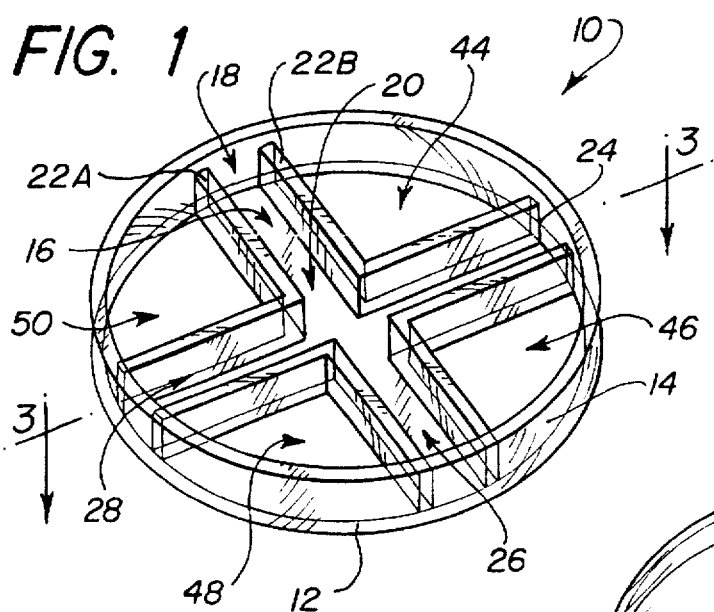
FIG. 1 is a perspective view of a motile channel pathogen detector constructed in accordance with the present invention.
Figure 3:
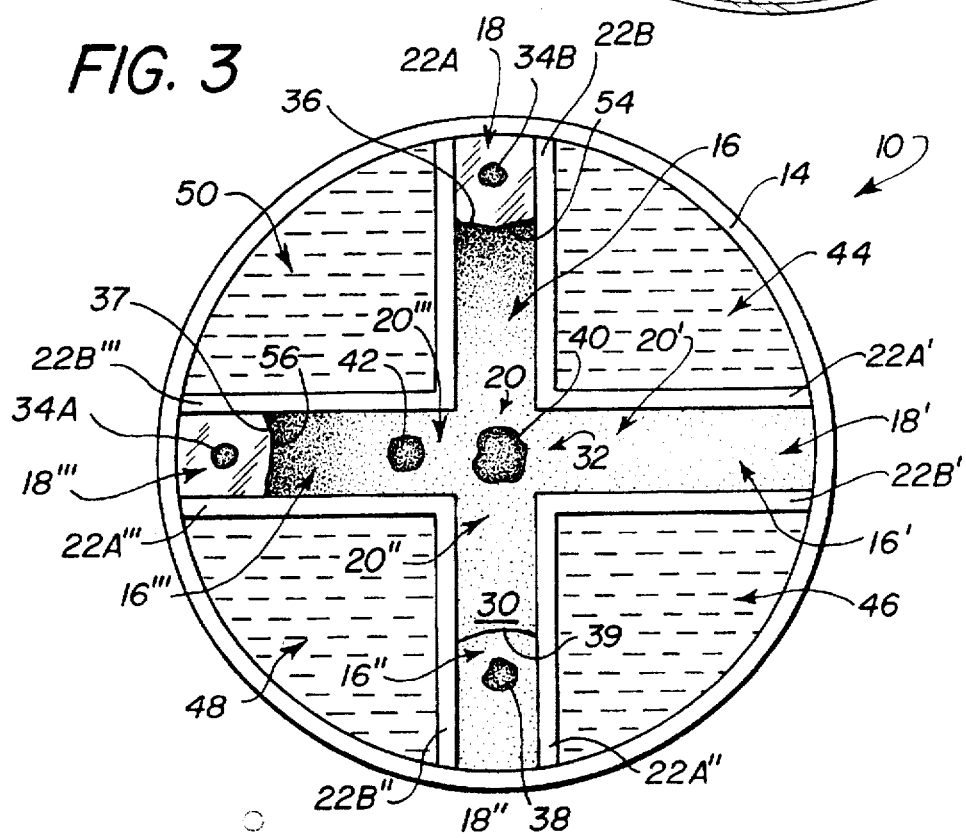
FIG. 3 is a plan view of the FIG. 1 motile channel pathogen detector taken along view line 3—3 of FIG. 1, showing schematic representations of components of the invention within the detector.

Referring to the drawings in detail, a motility channel pathogen detector of the present invention is shown in FIGS. 1 and 3, and generally designated by the reference numeral 10. As best seen in FIG. 1, the detector 10 includes a base 12 and an enclosure wall 14 arising from a peripheral edge of the base 12 to define a dish-like enclosure above the base 12, much like a traditional petri dish. A first motility channel 16 is defined along the base 12 and includes a first anti-serum end 18; a first inoculation end 20 opposed to the anti-serum end 18; and, opposed first channel walls 22A, 22B, so that the opposed first channel walls 22A, 22B cooperate to define the first motility channel 16 between the anti-serum and inoculation ends 18, 20 of the channel 16.

While the present invention may be in the form of a detector having only one motility channel (not shown), an alternative embodiment shown in FIGS. 1 and 3 includes a plurality of motility channels, hereinafter referred to as a second motility channel 24, third motility channel 26, and fourth motility channel 28. For convenience and to avoid confusion, the virtually identical components of the second, third and fourth motility channels 24, 26, 28 are referred to with the reference numerals of the first motility channel single, double and triple primed. Therefore as best seen in FIG. 3, for the second, third and fourth motility channels 24, 26, and 28, a second anti-serum end is 18', a third anti-serum end is 18" and a fourth anti-serum end is 18'''; a second inoculation end is 20', a third inoculation end is 20", and a fourth inoculation end is 20'''; and, opposed second channel walls are 22A', 22B', opposed third channel wall are 22A", 22B", and opposed fourth channel walls are 22A''', 22B'''.

The motility channel pathogen detector 10 also includes a growth medium means for supporting growth of a pathogen such as growth medium 30 positioned within the first, second, third and fourth motility channels 16, 24, 26, 28, and in a sample area 32 adjacent to and in fluid communication with the inoculation ends 20, 20', 20", 20''' of the channels. The growth medium 30 may be any standard growth medium commonly used and well-known in pathogen culture arts. A preferred growth medium 30 includes the following components with the following approximations of their respective concentrations listed in terms of units per liter of deionized or distilled water:

|   | INGREDIENT | CONCENTRATION |
|---|---|---|
| 1. | Proteose Peptone | 1–15 g. |
| 2. | Agar | 1–5 g. |
| 3. | Potassium Phosphate | $10^{-4}$–$10^{-2}$ moles |

Ingredient 1, the proteose peptone provides a nitrogen, carbon and energy source for the pathogen, and can be replaced by other well-known organic compounds (e.g., tryptones, peptones or a combination of any of the twenty common amino acids) or inorganic compounds (e.g., ammonium sulfate and glucose). Ingredient 2, the agar is a solidifying agent. Other common compounds such as agarose may also be used. Ingredient 3, the potassium phosphate maintains the pH of the medium, and it can be replaced by other buffering compounds, such as mono/dibasic potassium phosphate combinations or potassium phosphate adjusted to a pH of 6–9 with HCl or KOH solutions, etc.

A motility enhancing growth medium means for enhancing motility of pathogens may also be used, such as the aforesaid ingredients numbered 1–4, along with the following components and with the following approximations of their respective concentrations per liter of distilled or deionized water:

|   | INGREDIENT | CONCENTRATION |
|---|---|---|
| 4. | Magnesium Sulfate | 0.1–0.5 g. |
| 5. | EDTA | $1 \times 10^{-6}$–$5 \times 10^{-2}$ moles |
| 6. | L-methionine | $10^{-7}$–$10^{-5}$ moles |
| 7. | L-serine | $10^{-7}$–$10^{-2}$ moles |
| 8. | Sodium Deoxycholate | 0.05–1.0 g. |
| 9. | Potassium Tellurite | 0.1–10 mg. |

Ingredient 4, the magnesium sulfate is to enhance growth of the pathogen. Ingredient 5, the EDTA is a chelating agent for heavy metals. It can be omitted or replaced by other chelating agents. Ingredient 6, the L-methionine is to promote flagellar synthesis of motile pathogens. Ingredient 7, the L-serine is an attractant to enhance motility or chemotaxis of motile pathogens, and can be replaced and/or used in combination with DL-serine, or other amino acids (aspartate, glutamate, cysteine, alanine, glycine) dipeptides, carboxylic acids (malate, citrate), sugars (glucose galactose, ribose, fructose, fucose, mannose, trehalose maltose), sugar alcohols (mannitol, sorbitol), or amino-sugars (N-acetyl-D-glucosamine) that can react with the *E. coli* chemotactic transducers including a) soluble periplasmic substrate-binding proteins, such as the maltose system; b) cytoplasmic membrane transport components, such as the phosphotransferase system (PTS); and, c) primary chemotactic signal transducers including the methyl-accepting chemotactic proteins (MCP) such as the $T_{ar}$, $T_{sr}$, $T_{rg}$, $T_{ap}$ receptors. Non-metabolizable compounds such as α-methyl aspartate may also be used instead of the L-serine. Ingredient 8, the Sodium Deoxycholate inhibits gram-positive and non-enteric gram-negative bacteria. Other compounds with similar effects may be used, including weak acid organic dyes, such as bromthymol blue, phenol red, etc. Ingredient 9, the Potassium Tellurite is used to selectively enhance the survival of *E. coli* 0157:H7, and may be replaced or used in combination with other compounds well known in the art having the same effect, such as Novobiocin or cefiximine.

A pre-enriched motility enhancing growth medium means for enhancing motility of selectively enriched samples may also be used in the motility channels 16, 16', 16", 16'". The pre-enriched motility enhancing growth medium means includes the aforesaid ingredients numbered 1–7, but not ingredients numbered 8 (Sodium Deoxycholate) and 9 (Potassium Tellurite). When the sample of potential pathogens needs to be enriched to selectively increase a population of motile pathogens such as *E. coli* 0157:H7 before placement or inoculation of the sample in the motility channel pathogen detector 10, the sample is first placed for about 10–12 hours in a selective enrichment broth means for selectively increasing a population of motile pathogens, which selective enrichment broth means includes the following components with the following approximations of their respective concentrations listed in terms of units per liter of deionized or distilled water:

|   | INGREDIENT | CONCENTRATION |
|---|---|---|
| 10. | Proteose Peptone | 1.0–10.0 g. |
| 11. | Potassium Phosphate (pH 6–9) | $10^{-4}$–$10^{-2}$ moles |
| 12. | Lactose | 1.0–10.0 g. |
| 13. | Potassium Tellurite | 0.1–10 mg. |
| 14. | Sodium Novobiocin | 10.0–200.0 mg. |

The motility channel pathogen detector also includes anti-serum means for biologically interacting with a motile pathogen to restrict motility of the pathogen, such as *E. coli* H7 anti-serum, which is schematically represented in FIG. 3 at reference numerals 34A, 34B. *E. coli* H7 anti-serum is manufactured by DIFCO, Inc. of Detroit, Mich. As best seen in FIG. 3, the *E. coli* anti-serum 34A, 34B is positioned on the growth medium 30 within the anti-serum end of a motility channel, such as in the first and fourth anti-serum ends 18, 18'" of the first and fourth motility channels 16, 16'". The *E. coli* anti-serum 34A, 34B diffuses through the growth medium 30 to form a first anti-serum front 36 between the opposed channel walls 22A, 22B of the first motility channel 16, and to form a second anti-serum front 37 between the opposed channel walls 22A'", 22B'" of the fourth motility channel 16'". Another anti serum may be used in another of the motility channels, such as an anti serum generally referred to as "Salmonella H anti-serum Poly a-z", as manufactured by DIFCO, Inc. of Detroit, Mich. In the embodiment of detector 10 shown in FIG. 3, Salmonella H anti-serum Poly a-z is schematically represented at reference numeral 38 as being positioned in the third motility channel 16", while the second motility channel 16' has no anti-serum, thereby serving as a control. The Salmonella H anti-serum Poly a-z diffuses to form a third anti-serum front 39.

The motility channel pathogen detector 10 also includes a motile pathogen means for growing in the growth medium 30 and moving along the motility channels, such as a sample of potential pathogens including in the sample a target motile pathogen such as serotype of *Escherichia coli* bacteria referred to as "*E. coli* 0157:H7", or another bacteria commonly referred to as "Salmonella". The pathogen means is applied to the detector 10 in the form of a sample of potential pathogens including a target motile pathogen, and such a sample is schematically represented in FIG. 3 by reference numeral 40. The sample of potential pathogens 40 is positioned on the growth medium 30 in the sample area 32, so that potential pathogens may grow within the growth medium 30, and move away from the sample; into the first through fourth inoculation ends 20, 20', 20", 20'" of the first through fourth motility channels 16, 16', 16", 16'"; and through the four motility channels until any motile pathogens contact the first, second and third anti-serum fronts 36, 37, 39. In FIG. 3, the growth and motion of the motile pathogens is schematically represented by the partial shading, or "stippling" within the first through fourth motility channels 16, 16', 16", 16'" and the sample area 32.

In a further embodiment, the motility channel pathogen detector 10 may also include various polyvalent flagella anti-sera means positioned on the growth medium along any of the first through fourth motility channels for biologically interacting with any non-target or interfering motile pathogens and to thereby restrict the non-target pathogens from reaching the anti-serum front. For example, if it is desired to use the detector to detect as a target pathogen the specific motile pathogen E. coli 0157:H7 and E. coli anti-serum has been positioned within the detector 10 as in FIG. 3 within the first and fourth motility channels 16, 16'", then the polyvalent flagella anti-sera means may be positioned in one or more of the motility channels, such as in the fourth motility channel 16'" as represented schematically at reference numeral 42.

When the motile pathogens in the sample 40 move through the fourth motility channel 16'", the polyvalent flagella anti-sera 42 will diffuse in the growth medium so that non-target motile pathogens will biologically interact with the polyvalent flagella anti-sera 42 to stop movement of the non-target pathogens, thereby affording the E. coli 0157:H7 target pathogen more growth medium for its growth and hence movement between the position of the polyvalent flagella anti-sera 42 and the position of the second anti-serum front 37 in the fourth motility channel 16'". Consequently, the time necessary for the E. coli 0157:H7 target pathogen to reach the second anti-serum front 37 is reduced through use of the polyvalent flagella anti-sera means. The polyvalent flagella anti-sera means includes any compounds well-known in the art that biologically interact with non-target pathogens to restrict motility of the non-target pathogens without interrupting motility of a target pathogen.

Figure 2:
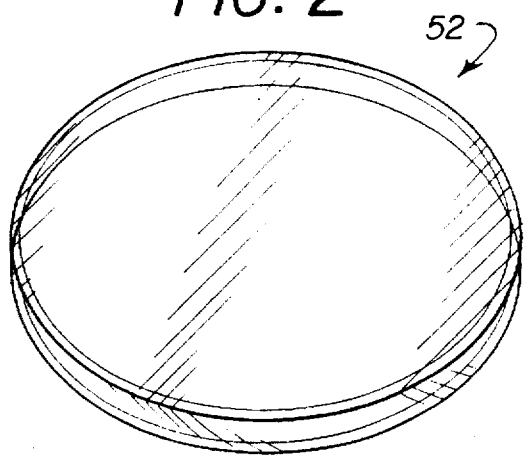
FIG. 2 is a perspective view of a cover for the FIG. 1 motile channel pathogen detector.

As seen best in FIGS. 1 and 3, the motility channel pathogen detector 10 also includes a moisture reservoir means for maintaining an enhanced humidity adjacent the four motility channels 16, 16', 16", 16'", such as first moisture reservoir 44, second moisture reservoir 46, third moisture reservoir 48, and fourth moisture reservoir 50. The moisture reservoir means is defined by the enclosure wall 14 and first through fourth opposed channel walls 22A, 22B, 22A', 22B', 22A", 22B", 22A'", 22B'" and a cover 52 (seen in FIG. 2) that is supported by the enclosure wall 14. The enclosure and channel walls are dimensioned so that the enclosure wall 14 extends over the channel walls (as seen in FIG. 1). Therefore, any liquid in the reservoir means cannot communicate with the growth medium 30 in the detector 10, but vapor leaving the reservoir means can pass over the channel walls, under the cover 14 to be adjacent the growth medium without leaving the detector 10.

The moisture reservoir means may be filled with any liquid appropriate for maintaining a stable moisture level adjacent the motility channels during incubation of the motile pathogens. In use of the moisture reservoir means, all four or any one or more of the moisture reservoirs 44, 46, 48, 50 are filled with a liquid such as distilled water, and the cover 52 (shown in FIG. 2) is placed over the detector 10 after positioning of the sample 40 of potential pathogens in the sample area. When the detector 10 is next placed in an oven for incubation, the liquid in the moisture reservoirs 44, 46, 48, 50 will evaporate to maintain a stable moisture level within and adjacent to the growth medium 30, thereby enhancing motility of the pathogens through the growth medium.

Tests have established that, in use of the motility channel pathogen detector 10 of the present invention, optimal results are obtained when a distance between the opposed channel walls is between 5 mm and 15 mm; a distance between a position of anti-serum placement and a position of placement of a motile pathogen means is between 30 mm and 35 mm; a depth of the growth medium is between 2 mm and 10 mm; an amount of anti-serum means (prepared according to a manufacturer's instructions) positioned in a motility channel is between 5 and 10 µµL; and an amount of sample of potential pathogen is between 10 and 20 µL.

In use of the motility channel detector 10 within the above parameters, after positioning of E. coli anti-serum and a sample containing only E. coli 0157:H7 in the sample area 32, and placement of distilled water within the moisture reservoir means, the cover 52 is positioned, and the detector is placed in an oven set between 22°–37° Centigrade for between 8–24 hours to allow the pathogen to grow and move through the four motility channels 16, 16', 16", 16'", as represented schematically in FIG. 3. The detector is then viewed for detection of any visible detection lines adjacent the anti-serum fronts 36, 36, 39. Such visible detection lines are distinctive in that they divide a region of pathogen growth from a region of no pathogen.

As best seen in FIG. 3, where E. coli 0157:H7 is the motile pathogen, a first visible detection line 54 appears adjacent the first anti-serum front 36 in the first motility channel 16 and a second visible detection line 56 appears adjacent the second anti-serum front 37 in the fourth motility channel 16'". The first and second visible detection lines 54, 56 separate areas of motile pathogen growth from areas of no pathogen growth in the first and fourth motility channels 16, 16'", as represented schematically in FIG. 3 by the presence and absence of shading or stippling in those channels 16, 16'". It is to be noted that the first, second and third anti-serum fronts 36, 37 and 39 may be invisible until visible detection lines form, or the anti-serum means may carry a coloring agent to facilitate detection of anti-serum fronts, as shown schematically in FIG. 3.

Where the sample of potential pathogens includes only E. coli 0157:H7, no visible detection line would form adjacent the third anti-serum front 39 in the third motility channel, because the Salmonella H anti-serum Poly a-z 38 does not biologically interact with the E. coli 0157:H7 pathogen, as shown in FIG. 3. In contrast, if the sample of potential pathogens included only Salmonella, a visible detection line (not shown) would form adjacent the third anti-serum front 39, and the first and second visible detection lines would not form, indicating the presence of only Salmonella. If visible detection lines appeared adjacent all three anti-serum fronts 36, 37, 39, the detector 10 would thereby indicate the presence of both E. coli 0157:H7 and Salmonella. If a visible detection line were to form in the second motility channel 16' which has no anti-serum means, it would be apparent that some contaminating agent in the growth medium had tainted the detector 10. The second motility channel 16' having no anti-serum means thereby serves as a control to invalidate such a test in the event of contamination.

In use of the motility channel pathogen detector 10 wherein the sample must be selectively enriched, the four motility channels 16, 16', 16", 16'" are filled with the pre-enriched motility enhancing growth medium means. The sample is exposed to the selective enrichment broth means in a standard procedure well-known in the art for about 10–12 hours, and then placed or inoculated in the sample area 32 of the detector 10. The detector is then incubated for an additional 10–26 hours at a temperature of between 22°–37° centigrade, and viewed as described above for detection of the first and second visible detection lines 54, 56. The motility channel pathogen detector 10 may be made of any materials capable of holding fluids, and is preferably made of materials that are transparent or translucent to enhance visibility such as glass, modern plastics, etc.

While the motility channel pathogen detector has been described and illustrated with respect to a particular construction, it is to be understood that the present invention is not to be limited to such examples. For example, the detector may include only one, or a plurality of motility channels. Accordingly, reference should be made primarily to the attached claims rather than the foregoing description.

We claim:

1. A motility channel pathogen detector for detecting a target motile pathogen in test sample of potential pathogens, comprising:
   a. a dish having a base and walls arising from the base to define a motility channel wherein the dish includes a moisture reservoir means adjacent the motility channel for maintaining an enhanced humidity;
   b. an anti-serum end of the motility channel;
   c. an inoculation end of the motility channel opposed to the anti-serum end;
   d. opposed channel walls that cooperate to define the motility channel between the anti-serum end and inoculation end of the motility channel;
   e. a growth medium in the motility channel;
   f. an anti-serum that biologically interacts with the target motile pathogen, the anti-serum being positioned in the growth medium in the anti-serum end so that the anti-serum diffuses in the growth medium to form an anti-serum front between the channel walls; and
   g. wherein when said target motile pathogen is positioned in the growth medium adjacent the inoculation end the target motile pathogen moves towards, contacts and accumulates adjacent the anti-serum front to form a visible detection line adjacent the anti-serum front.

2. The motility channel pathogen detector of claim 1, wherein the growth medium further comprises a motility enhancing growth medium means for enhancing motility of pathogens.

3. The motility channel pathogen detector of claim 2, wherein the motility enhancing growth medium means comprises the following compounds in one liter of distilled water:
   a. 1–15 g. of Proteose Peptone;
   b. 1–5 g. of Agar;
   c. $10^{-4}$–$10^{-2}$ moles of Potassium Phosphate;
   d. 0.1–0.5 g. of Magnesium Sulfate;
   e. $1\times10^{-6}$–$5\times10^{-2}$ moles of EDTA;
   f. $10^{-7}$–$10^{-5}$ moles of L-methionine;
   g. $10^{-7}$–$10^{-2}$ moles of L-serine;
   h. 0.05–1.0 g. of Sodium Deoxycholate; and
   i. 0.1–10 mg. of Potassium Tellurite.

4. The motility channel pathogen detector of claim 1, wherein the anti-serum further comprises anti-serum means for biologically interacting with a motile pathogen to restrict motility of the pathogen.

5. The motility channel pathogen detector of claim 4, wherein the anti-serum means comprises E. coli H7 anti-serum.

6. The motility channel pathogen detector of claim 1, wherein a polyvalent flagella anti-serum means for biologically interacting with non-target motile pathogens is positioned on the growth medium within the motility channel between the anti-serum and the inoculation ends of the motility channel.

7. The motility channel pathogen detector of claim 1 wherein a distance between the opposed channel walls is between 5 mm and 15 mm; a distance between a position of anti-serum placement and a position of placement of a motile pathogen means is between 30 mm and 35 mm; a depth of the growth medium is between 2 mm and 10 mm; an amount of anti-serum means positioned in a motility channel is between 5 and 10 μL; and an amount of the sample of potential pathogen is between 10 and 20 μL.

8. The motility channel pathogen detector of claim 1, wherein the detector comprises a plurality of motility channels.

9. The motility channel pathogen detector of claim 8, wherein one of the plurality of motility channels has no anti-serum.

10. A method of detecting a target motile pathogen from a sample of potential pathogens, comprising the steps of:
    a. positioning an anti-serum means on a growth medium within an anti-serum end of a motility channel in the motility channel pathogen detector of claim 1, the anti-serum means being for biologically interacting with a motile pathogen to restrict motility of the pathogen so that the anti-serum means diffuses to form an anti-serum front between opposed channel walls of the anti-serum end of the motility channel;
    b. inoculating the sample of potential pathogens on the growth medium adjacent an inoculation end of the motility channel opposed to the anti-serum end;
    c. incubating the detector having the positioned anti-serum means and sample of potential pathogens at between 22 and 37 degrees centigrade for between 8 and 24 hours; and
    d. viewing the anti-serum end of the incubated detector for accumulation of the target motile pathogens into a visible detection line adjacent the anti-serum front.

11. The method of claim 10, wherein the positioning of anti-serum means and inoculating the sample steps are preceded by the further steps of preparing a motility enhancing growth medium means for enhancing motility of the target motile pathogen, and placing the motility enhancing growth medium means within the motility channel of the motile channel pathogen detector.

12. The method of claim 10, wherein the incubating step is preceded by the further step of positioning a polyvalent flagella anti-serum means for biologically interacting with non-target motile pathogens on the growth medium within the motility channel between the anti-serum and inoculation ends of the motility channel.

13. The method of claim 10, wherein the step of positioning the anti-serum means comprises the further step of positioning E. coli H7 anti-serum in the anti-serum end of the motility channel.

14. The method of claim 10, wherein the incubating step is preceded by the further steps of filling a moisture reservoir means in the detector with a liquid for maintaining an enhanced humidity adjacent the motility channel and then placing a cover over the detector.

15. The method of claim 10, wherein the positioning of anti-serum means and inoculating the sample steps are preceded by the further steps of preparing a pre-enriched motility enhancing growth medium means for enhancing motility of selectively enriched samples of potential pathogens, placing the pre-enriched motility enhancing growth medium means in the motility channel, and placing the sample in a selective enrichment broth means for selectively increasing a population of the target motile pathogen in the sample for about 10–12 hours.

16. A motility channel pathogen detector for detecting a target motile pathogen in a sample of potential pathogens, comprising:

a. a dish having a base and walls arising from the base to define a motility channel wherein the dish includes a moisture reservoir means adjacent the motility channel for maintaining an enhanced humidity;

b. an anti-serum end of the motility channel;

c. an inoculation end of the motility channel opposed to the anti-serum end;

d. opposed channel walls that cooperate to define the motility channel between the anti-serum end and inoculation end of the motility channel;

e. a growth medium means positioned in the motility channel for supporting growth of potential pathogens;

f. an anti-serum means for biologically interacting with the target motile pathogen to restrict motility of the target motile pathogen, the anti-serum being positioned in the growth medium in the anti-serum end so that the anti-serum diffuses in the growth medium to form an anti-serum front between the channel walls; and g. wherein when said target motile pathogen is positioned in the growth medium adjacent the inoculation end so that the target motile pathogen moves towards, contacts and accumulates adjacent the anti-serum front to form a visible detection line adjacent the anti-serum front.

17. The motility channel pathogen detector of claim 16, wherein the growth medium means further comprises a motility enhancing growth medium means for enhancing motility of pathogens.

18. The motility channel pathogen detector of claim 17, wherein a polyvalent flagella anti-serum means for biologically interacting with non-target motile pathogens is positioned on the growth medium within the motility channel between the anti-serum and the inoculation ends of the motility channel.

19. The motility channel pathogen detector of claim 16, wherein the detector comprises a plurality of motility channels.

20. The motility channel pathogen detector of claim 19, wherein one of the plurality of motility channels has no anti-serum.

21. The motility channel pathogen detector of claim 20, wherein a distance between the opposed channel walls is between 5 mm and 15 mm; a distance between a position of anti-serum placement and a position of placement of a motile pathogen means is between 30 mm and 35 mm; a depth of the growth medium is between 2 mm and 10 mm; an amount of anti-serum means positioned in a motility channel is between 5 and 10 µL; and an amount of sample of potential pathogen is between 10 and 20 µL.

* * * * *